(12) United States Patent
Botten

(10) Patent No.: US 9,116,887 B2
(45) Date of Patent: Aug. 25, 2015

(54) MEDICINAL SUBSTANCE RECOGNITION SYSTEM AND METHOD

(76) Inventor: Peter O Botten, Lakewood, OH (US)

( * ) Notice: Subject to any disclaimer, the term of this patent is extended or adjusted under 35 U.S.C. 154(b) by 0 days.

(21) Appl. No.: 13/404,766

(22) Filed: Feb. 24, 2012

(65) Prior Publication Data

US 2013/0221082 A1   Aug. 29, 2013

(51) Int. Cl.
*G06F 17/00* (2006.01)
*G06F 17/30* (2006.01)
*G06F 19/00* (2011.01)

(52) U.S. Cl.
CPC ............ *G06F 17/30* (2013.01); *G06F 19/3456* (2013.01)

(58) Field of Classification Search
USPC ............... 235/375, 454, 462.01, 494, 462.14, 235/462.45, 472.01; 705/2, 3
See application file for complete search history.

(56) References Cited

U.S. PATENT DOCUMENTS

| | | | | |
|---|---|---|---|---|
| 5,700,998 A * | 12/1997 | Palti | ............................... | 235/375 |
| 5,774,865 A * | 6/1998 | Glynn | ................................ | 705/2 |
| 5,992,742 A * | 11/1999 | Sullivan et al. | .......... | 235/462.01 |
| 6,776,341 B1 * | 8/2004 | Sullivan et al. | .......... | 235/462.01 |
| 6,799,725 B1 * | 10/2004 | Hess et al. | ............... | 235/462.01 |
| 6,932,272 B1 * | 8/2005 | Liu et al. | .................. | 235/462.01 |
| 7,059,526 B1 * | 6/2006 | Sullivan et al. | .......... | 235/462.01 |
| 7,369,919 B2 * | 5/2008 | Vonk et al. | ..................... | 700/236 |
| 7,370,795 B2 * | 5/2008 | Radatti et al. | ................. | 235/381 |
| 7,370,797 B1 * | 5/2008 | Sullivan et al. | .......... | 235/462.01 |
| 2006/0088196 A1 * | 4/2006 | Popovich et al. | ............ | 382/128 |
| 2007/0000805 A1 * | 1/2007 | Van Den Brink | ............. | 206/531 |
| 2007/0189597 A1 * | 8/2007 | Limer et al. | .................. | 382/153 |
| 2008/0000979 A1 * | 1/2008 | Poisner | .................... | 235/462.01 |
| 2008/0056556 A1 * | 3/2008 | Eller et al. | ..................... | 382/142 |
| 2008/0298603 A1 * | 12/2008 | Smith | ............................. | 381/67 |
| 2009/0129556 A1 * | 5/2009 | Ahn | ............................. | 378/208 |
| 2009/0299522 A1 * | 12/2009 | Savir et al. | ..................... | 700/240 |
| 2011/0054935 A1 * | 3/2011 | Hardaway | ......................... | 705/3 |
| 2011/0113730 A1 * | 5/2011 | Aylward | ......................... | 53/432 |
| 2012/0043475 A1 * | 2/2012 | Ahn | .......................... | 250/453.11 |
| 2013/0142406 A1 * | 6/2013 | Lang et al. | .................... | 382/128 |
| 2013/0197693 A1 * | 8/2013 | Kamen et al. | ................ | 700/244 |

* cited by examiner

*Primary Examiner* — Tuyen K Vo
(74) *Attorney, Agent, or Firm* — Pearne & Gordon LLP

(57) ABSTRACT

Provided is an apparatus for identifying a medicinal substance. A tray receives and concurrently supports a plurality of pills formed at least in part from the medicinal substance. A computer-readable memory stores a drug database including one or more identifying features for identifying different pills formed at least in part from different medicinal substances. A recognition device is arranged to interrogate the pills on the tray and detect at least one of the identifying features from the pills. A controller receives the identifying feature(s) detected by the recognition device and determines the identity of the medicinal substance from among the different medicinal substances in the drug database based on the identifying feature(s).

19 Claims, 6 Drawing Sheets

MEDICINAL SUBSTANCE RECOGNITION SYSTEM AND METHOD

BACKGROUND OF THE INVENTION

1. Field of the Invention

This application relates generally to a method and apparatus for detecting a medicinal substance and, more specifically, to method and apparatus for optically identifying and optionally counting individual units of a medicinal substance with a computer apparatus.

2. Description of Related Art

Traditional methods of dispensing drugs require a pharmacist to manually retrieve a container storing the drug to be dispensed. The container is typically stored on a shelf with many other containers storing different drugs, requiring the pharmacist to select the proper container based on the human-readable label content appearing on each label. Once a container has been retrieved, the pharmacist removes tablets, capsules or other units of a drug in solid form (generally referred to herein as "pills") from the container and the desired quantity to be dispensed manually counted by the pharmacist.

Pharmacists will perform such a procedure many times throughout a workday. The frequent repetition of this procedure can cause fatigue to set in, possibly causing the pharmacist to confuse a prescribed quantity of one drug with the prescribed quantity of another drug. Further, the pharmacist may misread the label content on a container, resulting in the wrong drug being dispensed.

BRIEF SUMMARY OF THE INVENTION

Accordingly, there is a need in the art for a method and apparatus that recognizes a drug, and optionally a quantity of the drug being dispensed.

According to one aspect, the subject application involves an apparatus for identifying a medicinal substance. A tray receives and concurrently supports a plurality of pills formed at least in part from the medicinal substance. A computer-readable memory stores a drug database including one or more identifying features for identifying different pills formed at least in part from different medicinal substances. A recognition device is arranged to interrogate the pills on the tray and detect at least one of the identifying features from the pills. A controller receives the identifying feature(s) detected by the recognition device and determines the identity of the medicinal substance from among the different medicinal substances in the drug database based on the identifying feature(s).

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
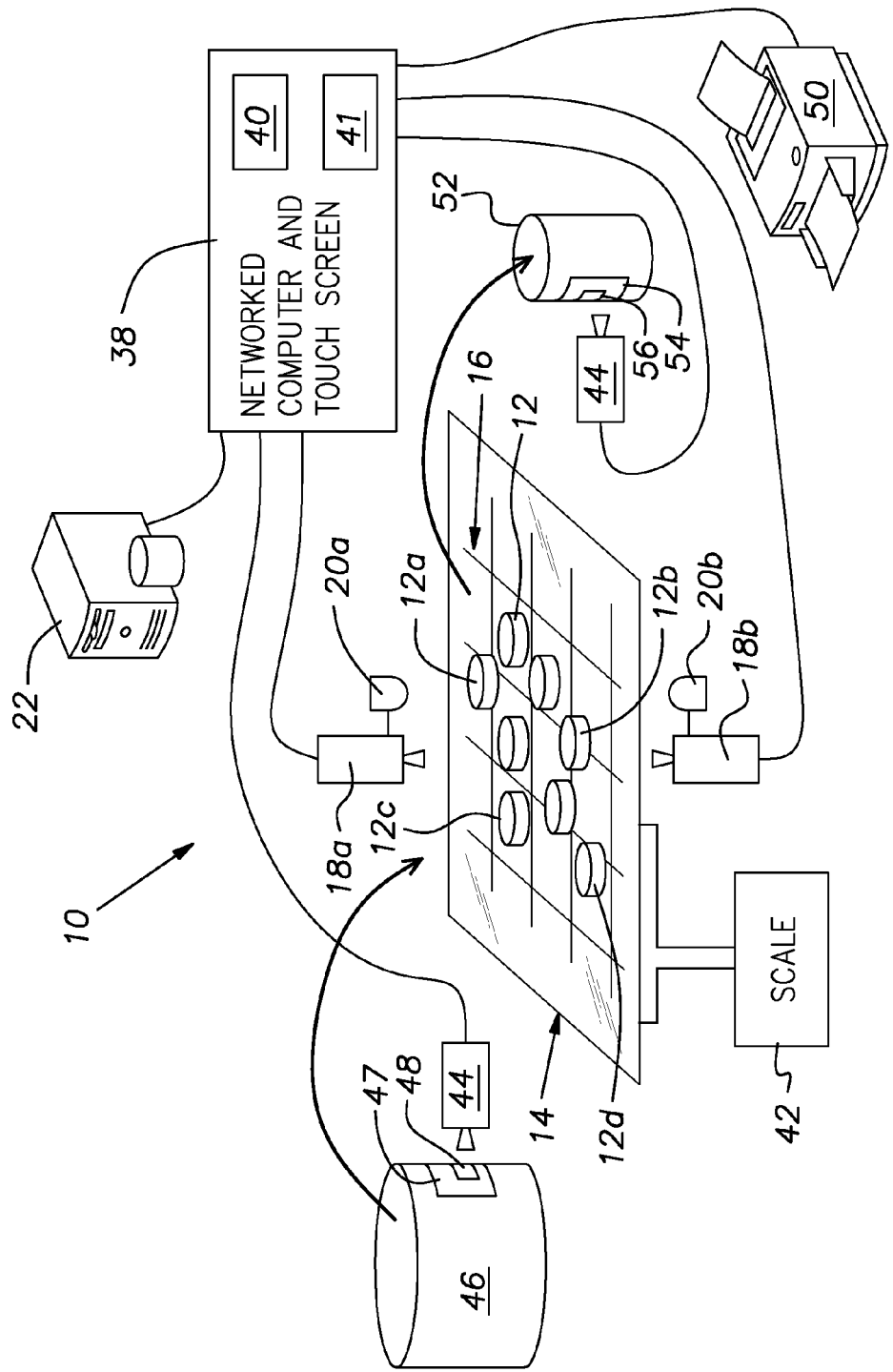
FIG. 1 is a schematic illustration of an identification apparatus for identifying a medicinal substance included in a pill to be distributed to a patient.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

FIG. 1 shows a schematic illustration of an identification apparatus 10 for identifying a medicinal substance included in pills 12 to be distributed to a patient. For the sake of brevity, the illustrative embodiments of the identification apparatus 10 are described herein as being utilized in a pharmacy to dispense pills including a medicinal substance prescribed by a physician to a patient. However, it is to be understood that the identification apparatus 10 can be employed in any environment where individual identification of pills 12 is useful without departing from the scope of the present invention.

For the embodiment shown in FIG. 1, the identification apparatus 10 includes a tray 14 that receives, and concurrently supports, a plurality of the pills 12 thereon. Each of the pills 12 is formed at least in part from a medicinal substance, and optionally a combination of medicinal substances. The pills 12 themselves can possess one or more identifying features that can be used to identify the medicinal substance(s) included therein. The identifying features can include: a physical property such as a shape, size, color, weight, density, one or more characters appearing on an exterior surface of each of the pills 12, other physical properties of the pills 12, or any combination thereof; a chemical property such as luminescence exhibited by the pills 12 in response to be exposed to light having a single wavelength or a plurality of different wavelengths, any other chemical property, or a combination thereof; or a combination of one or more physical properties and one or more chemical properties.

The tray 14 can be formed from any suitable material, and can optionally have a substantially-planar appearance as shown in FIG. 1, or optionally have a cupped or bowl-shaped appearance, or any other desired shape that can support the desired number of pills 12 thereon. The substantially-planar surface provided to the tray 14 in FIG. 1, however, allows the pills 12 to be distributed thereon in a single layer. Distributing the pills 12 in a single layer promotes optical recognition of the pills 12 on the tray 14 by minimizing the number of pills 12 that are "buried" or otherwise concealed from view by the one or more recognition devices 18 discussed below. The tray 14 can be a substantially transparent glass plate that is devoid of any markings, or can optionally include a marking system 16 to act as a reference for detecting a physical property of the pills 12 on the tray. For example, the marking system 16 can optionally include a grid pattern including spaced graduations such as that shown in FIG. 1 having spaces with a known dimension between individual lines. Major lines can be spaced apart by a first distance such as one (1 cm) centimeter, and optionally separated by minor graduation lines that are separated from each other by a second, smaller distance such as one (1 mm) millimeter. Further, the marking system, regardless of the types of graduations, can along one or two axes, such as the X and/or Y axes of the tray 14, for example. Regardless of the form of the marking system 16, the graduations provide a reference for measuring at least one of the dimensions (i.e., size) and the shape of the pills 12 while on the tray 14.

The marking system 16 can be painted or otherwise applied to a surface of the tray 14, can be molded from a material that contrasts with a material from which the tray 14 is formed, can be projected onto the tray 14 as a light pattern, or otherwise made visible to a recognition device 18 described below.

The identification apparatus 10 in FIG. 1 also includes at least one, and optionally a plurality of recognition devices 18a, 18b (the recognition device(s) being referred to generally herein at 18) arranged to interrogate the pills 12 on the tray 14 and detect at least one of the identifying features from those pills 14 while they are on the tray 14. The recognition device(s) 18 can be any device that can sense one or more of the identifying features, and can be an active or a passive device. For example, each recognition device 18 can be independently selected as a digital camera, for example, that can capture a digital image of the pills 12 on the tray 14 from a known vantage point. For embodiments utilizing a tray 14 without the marking system 16, the position of the digital cameras as the recognition device(s) 18 can be fixed at known locations. For such embodiments, a scaling algorithm can be included in, or otherwise utilized with computer-executable instructions that are executable by a processing component of a controller 38 discussed below to optically recognize and optionally count the pills 12 on the tray 14. The computer-executable instructions to be executed by the processing component for performing the optical recognition process can also optionally factor in parameters including, but not limited to, the lens of each digital camera, the sensor of each digital camera, the image processing system of each digital camera, the location of each digital camera relative to the tray 14 or pills 12, or any combination thereof. Yet other embodiments can use features such as the luminescence of the pills 12 in response to being illuminated by light of a known wavelength, or other such features that are detectable without using the marking system 16 as a reference. Thus, the embodiments including a tray 14 without the marking system 16 recognize the pills 12 on the tray 14 independent of the marking system 16 (i.e., based solely on the physical, chemical, luminescent and possibly other features of the pills 12 themselves captured by the digital cameras and any other recognition device 18 present). According to other embodiments, the digital image captured by the recognition device 18 can optionally include at least a portion, and optionally all of the marking system 16 that is provided to the tray 14 at a location to be visible to the recognition device 18. To clearly describe the present invention, an embodiment of the identification apparatus 10 is shown in FIG. 1 and described in detail below as utilizing the marking system 16 to aid in the identification of the pills 12. However, it is understood that the present invention is not so limited, and can recognize the pills 12 on the tray 14 without reference to the marking system 16.

According to alternate embodiments, the digital camera or other suitable recognition device 18 can optionally detect different luminescence responses exhibited by the pills 12 when subjected to a known wavelength, or a plurality of different known wavelengths of light. For such embodiments one, or optionally a plurality of illumination sources 20a, 20b (referred to generally at 20) can be arranged to impart the light of the desired wavelength(s) onto the pills 12 on the tray 14. The illumination sources 20 can optionally include a variable-wavelength source of light having different wavelengths, can be a fixed-wavelength source of light having a single wavelength, or both. For embodiments where a plurality of different wavelengths are used to illuminate the pills 12, the recognition device(s) can optionally include a sensor that detects the luminescent response of the pills 12 as an identifying feature using multi-wavelength spectroscopy.

The embodiment shown in FIG. 1 includes both an upper recognition device 18a and a lower recognition device 18b. The upper recognition device 18a is arranged adjacent to an upper illumination source 20a to interrogate the pills 12 on the tray 14 from a vantage point located at an elevation vertically above the tray 14. The lower recognition device 18b is arranged adjacent to a lower illumination source 20b to interrogate the pills 12 on the tray 14 from a vantage point located at an elevation vertically below the tray 14. For such an embodiment, a portion of the tray 14 can be formed from a material that is substantially transparent to the lower recognition device 18b, the lower illumination source 20b, or both. Accordingly, the lower recognition device 18b, either alone or with the assistance of the lower illumination source 20b, can interrogate the pills 12 on the tray 14, through the transparent portion of the tray 14, from a vantage point below the tray 14.

A non-transitory computer-readable memory 22, which can be a magnetic or solid-state hard disk drive, optical medium such as a CD, or other suitable storage device stores a drug database comprising a plurality of drug entries. Each drug entry includes one or a plurality of identifying features of a pill 12 related to a specific medicinal-substance makeup of that pill 12. For example, a drug entry for oxycodone may be included in the drug database. A variety of drug-specific information can be included in the oxycodone drug entry, and each drug entry can optionally be specific to a particular dosage, source such as a manufacturer/repackager.

Figure 2:
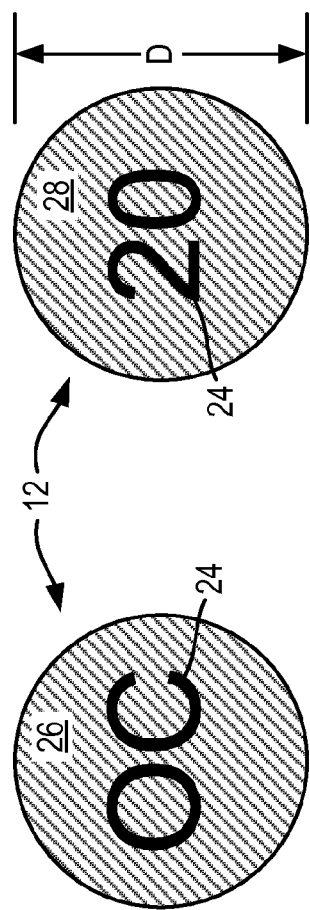
FIG. 2 is a schematic representation of first and second major surfaces of a first pill formed at least in part from a first medicinal substance.

Continuing with the oxycodone example with reference to FIG. 2, a drug entry for a pill 12 containing a 20 mg dose of oxycodone can include information such as: the dosage of oxycodone in a pill (e.g., 20 mg), the color of a 20 mg oxycodone pill (e.g., pink), the physical shape of a 20 mg oxycodone pill (e.g., round), one or more dimensions of the specific shape of a 20 mg oxycodone pill (e.g., diameter D=7 mm), a character such as an imprint 24 appearing on a 20 mg oxycodone pill (e.g., "OC" on a first major side 26 and "20" on an opposite major side 28), a weight of each 20 mg oxycodone pill, any other suitable identifying feature, or any combination thereof.

Figure 3:
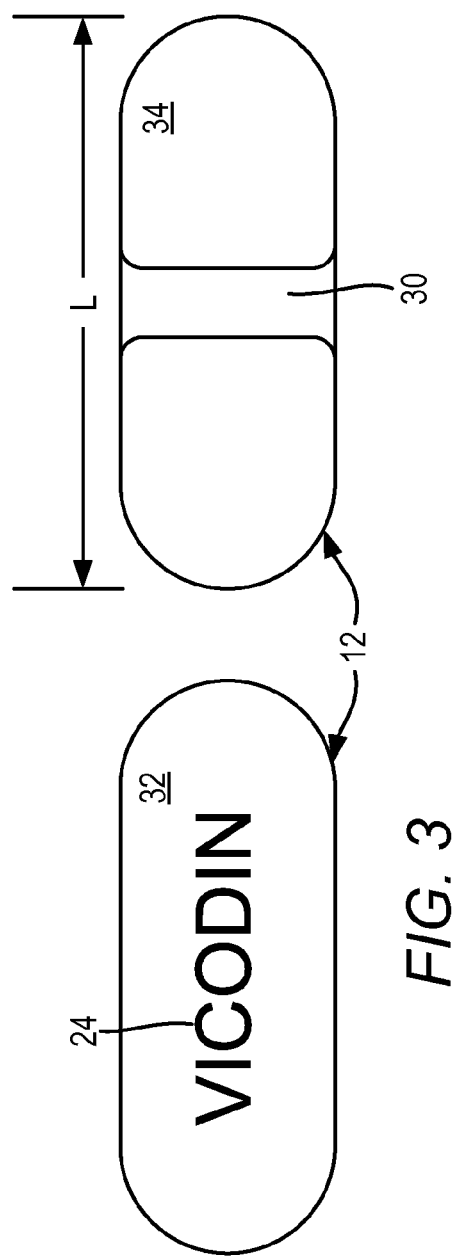
FIG. 3 is a schematic representation of first and second major surfaces of a second pill formed at least in part from a second medicinal substance, other than the medicinal substance from which the pill appearing in FIG. 2 is formed.

Another drug entry in the drug database can be an entry for a combination of medicinal substances, such as acetaminophen/hydrocodone, commonly referred to by its trade name Vicodin, for example. A pill 12 containing 500 mg/5 mg dose of acetaminophen/hydrocodone, respectively, is shown in FIG. 3. As shown, the pill 12 has the following identifying features that can be stored in the drug entry for 500 mg/5 mg dose of acetaminophen/hydrocodone in the drug database: the color of the pill (e.g., white), the physical shape of the pill (e.g., elliptical/oval), one or more dimensions of the pill with that shape (e.g., length L=17 mm), a character such as an imprint 24 appearing on the pill (e.g., "VICODIN" on a first major side 32) and a structural feature (e.g., a scoreline 30 that facilitates breakage of the pill 12 at a known location formed an opposite major side 34), any other suitable identifying feature, or any combination thereof.

Although the imprint 24 appearing in FIGS. 2 and 3 includes characters indicative of the identity of the medicinal substance and the dosage, other embodiments of the imprint can include any physical markings that can serve to distinguish a first pill from a second, different pill. For example, a logo or trademark of a manufacturer/repackager or other source of the pill can serve as the imprint 24.

In addition to the identifying features, each entry in the drug database can optionally also include additional information about the respective medicinal substance(s). For example, each drug entry can include a code or other identification number such as the National Drug Code ("NDC") or Universal Product Code ("UPC") associated with the respective medicinal substance(s), for example. Another example of the additional information includes a generic name, a trade name or common name by which the medicinal substance is known.

With reference once again to FIG. 1, the identification apparatus 10 also includes a controller 38, which can optionally be provided with a user interface 40 for presenting information such as a confirmation notice, a warning, any other information pertinent to the distribution of the pills 12, or any combination thereof, to a user. The user interface 40 can include a display device, a speaker, or other output interface that can visually, audibly, or both visually and audibly present such information to the user. The controller 38 also includes a computer processor 41 that is operable to execute computer-executable instructions to form a processing component that performs the functions described herein as being performed by the controller 38.

The controller 38 receives at least one identifying feature detected by the one or more recognition device(s) 18 via a local connection such as over a USB or other suitable cable; via communication network, which can include a local area network ("LAN"), wide area network ("WAN"), or a combination of a LAN and a WAN; or via any other suitable communication channel or combination thereof. The controller 38 compares the identifying feature(s) received to the identifying feature(s) stored for each drug entry in the drug database to identify a drug entry with identifying feature(s) that match those detected by the recognition device(s) 18. Accordingly, the controller 38 determines the identity of the medicinal substance(s) included in the pills 12 from among the different medicinal substances in the drug database based on the identifying feature(s) detected by the recognition device(s) 18.

The computer-readable memory 22 is shown in FIG. 1 as part of a network connected database server to which the controller 38 is connected via a LAN, WAN, or LAN and WAN network connection. However, other embodiments can include a computer-readable memory 22 provided internally of, or locally connected to the controller 38, making the identification system 10 a stand-alone, fully operational and self-contained apparatus. Each such local apparatus could operate by accessing its own drug database rather than sharing a drug database with another apparatus. Alternatively, a plurality of identification apparatuses located at a common physical location (e.g., a specific pharmacy) can optionally share a common drug database via a LAN, simplifying maintenance and upkeep of the common drug database for that physical location. Making the computer-readable memory 22 network accessible allows for the drug database to be created, maintained and updated centrally to be accessed by a plurality of different identification stations.

A scale 42 can optionally be coupled to the tray 14 to weigh the pills 12 on the tray 14. The scale 42 can optionally be tared before placement of the pills 12 on the tray 14 so that as pills 12 are removed the weight of the pills 12 remaining on the tray 14 can provide an indication of the quantity removed. The controller 38 can retrieve the weight of each pill 12 identified based on the identifying feature(s) detected by the recognition device(s) 18 from the respective entry of the drug database or another computer-readable memory. Thus, the overall weight of the pills 12 on the tray 14 can be divided by the known weight of each pill 12 retrieved by the controller 38 to calculate the number of pills 12 on the tray 14. According to alternate embodiments, the recognition device(s) 18 can optionally capture image data representing the pills 12 on the tray 14 and transmit such image data to the controller 38. In turn, the processor component provided to the controller 38 can execute computer-executable instructions to perform a recognition process that counts the number of pills 12 from the image data. The controller 38 can optionally determine the number of pills 12 present using only the weight-based approach based on the weight measured with the scale 42, using only the image approach based on the image data captured by the recognition device(s), or use both the weight-based approach and the image approach for redundancy.

One scanner 44, or optionally a plurality of scanners 44 can be included as part of the identifying apparatus 10 to interrogate and a machine-readable code such as a barcode, RFID tag, etc. . . . , to extract information encoded by such a code. For example, the scanner 44 can be a barcode scanner that optically interprets an arrangement of lines or points for 1-dimensional ("1D") or 2-dimensional ("2D") barcodes, respectively. The barcode scanner converts the interpretation of the symbols forming the barcode into a signal that is to be received by the controller 38. The computer processor 41 of the controller 38 executes computer-executable instructions to determine the information encoded by the barcode based on the signal received from the barcode scanner. To clearly describe the embodiment shown in FIG. 1, the scanner 44 will be described as a barcode scanner 44 hereinafter, but any type of scanner that can interrogate a machine-readable code and transmit a signal indicative of the encoded information is within the scope of the present invention.

For the embodiment illustrated in FIG. 1, a bulk container 46 storing the pills 12 to be dispensed to a patient is labeled with a barcode 48 as the machine-readable code. The bulk container 46 can be brought into close proximity of the barcode scanner 44 such that the barcode 48 is exposed to an optical detector provided to the barcode scanner 44. The optical detector detects the pattern of symbols that collectively form the barcode 48 and the detected pattern is converted into a signal to be transmitted by the barcode scanner 44 and eventually received by the controller 38. The barcode 48 can store encoded information such as the identity of the medicinal substance stored in pill form within the bulk container 46, the dosage of the medicinal substance in those pills, an expiration date of those pills, a quantity of those pills remaining in the bulk container 46, any other information pertaining to those, or any combination thereof. The barcode can be interrogated by the barcode scanner 44, which then generates a signal indicative of a portion, or all of the information encoded by the barcode 48 and transmits the signal to be received and interpreted by the controller 38, optionally by the computer processor 41 executing computer-executable instructions.

For example, the computer processor 41 can be operable to interpret the signal transmitted by the barcode scanner 44 by decoding the information encoded by the barcode represented by the signal. The decoded information can be compared to corresponding information in a plurality, or all of the drug entries in the drug database to identify any matching information. For instance, the name of the medicinal substance in the pills 12 and the dosage of such pills can be extracted by the controller 38 based on the signal transmitted by the barcode scanner 44. The controller 38, through operation of the computer processor 41, can query the drug database to identify a drug entry having a matching medicinal substance name and dosage, and return that name and dosage as a result of the query to notify the user of the identifying system of the identity of the pills 12 based on the barcode 48. The notification can be performed audibly, visually, or both audibly and visually via the user interface 40 operatively coupled to the controller 38. The notification can optionally be presented along with a confirmation request that instructs the user to manually compare the information contained in the notification presented via the user interface 40 with human-readable information (i.e., information presented in word form using alphabetic, numeric, or alpha-numeric characters that are readable by the human eye without the assistance of a computer) appearing on a label 47 provided to the bulk container 46. The notification can optionally be accompanied by a confirmation entry display shown by a touch-screen or other suitable display device. To continue with the process, the user can optionally be required to touch a selectable option on the touch-screen display (or use a computer peripheral such as a keyboard or mouse to select a selectable option presented on a display that is not touch sensitive) confirming the consistency between the human-readable information and the information presented to the user based on interrogation of the machine-readable code 48 with the scanner 44.

The identifying apparatus 10 can also include a printer 50 or other code-producing device such as a RFID tag programmer and the like, that generates an identifier including a machine-readable code (interchangeably referred to herein as a "computer-readable code") an output to be applied to, or otherwise accompany a patient container 52 in which the pills 12 on the tray, or a portion thereof, are to be delivered to the patient. The identifier can be a patient label 54 including the machine-readable code 54 to be adhesively applied to the patient container 52. Such a machine-readable code 54 can encode information such as the identity of the medicinal substance found in the pills 12 to be placed within the patient container 52 and delivered to the patient, a dosage of such pills 12, a quantity of the pills 12 to be delivered to the patient in the patient container 52, any other information pertaining to the pills 12 to be delivered to the patient in the patient container 52, or any combination thereof.

The printer 50 can print the lines, pixels or other symbols used to collectively form a 1D or 2D barcode 56 on the label 54 to be adhered to the patient container 52 according to the embodiment in FIG. 1. For an embodiment that utilizes RFID technology, however, the code-producing device can include a transmitter that conducts a current through a coil to induce a corresponding current in an RFID tag that is to be applied to, or otherwise accompany the patient container 52. Of course other machine-readable codes for labeling the patient container 52 can be generated by any corresponding output device capable of producing the machine-readable code is within the scope of the present invention.

The computer processor 41 of the controller 38 can optionally execute computer-executable instructions stored in a non-transitory computer memory to as a warning component to issue a warning to the user of the identifying apparatus 10 if a discrepancy is detected. For example, the warning component can issue an alert when conflicting medicinal substances and/or dosages are identified based on the identifying feature(s) detected by the recognition device(s) 18 and based on interrogation of the machine-readable code 48, for example. In other words, if the identity of the medicinal substance, the dosage, or both the identity of the medicinal substance and the dosage determined by the controller 38 based on the barcode 48 does not match the same information determined by the controller 38 based on the signal(s) from the recognition device(s) 18, the warning component can issue an alert.

The warning component can issue an alert in response to any inconsistency between the information determined based on the identifying feature(s) of the pills 12 on the tray 14 and any other information available to the identifying apparatus 10. For example, the user can optionally be required to manually enter information pertaining to the pills 12 using the user interface 40, a computer input peripheral such as a keyboard and a mouse, or any combination thereof. For instance, the identity of the medicinal substance may be obtained from the drug database based on the identifying feature(s) of the pills 12 detected by the recognition device(s) 18, but perhaps the identifying feature(s) were insufficient or otherwise did not indicate a dosage. The identity of the medicinal substance can optionally be presented to the user via the user interface 40 along with a request to enter the dosage of the medicinal substance to be dispensed in pill form to the patient. If the entered dosage does not match the dosage determined by the controller 38 based on interrogation of the barcode 48, the warning component can issue an alert to the user, bringing the discrepancy to the user's attention.

As another example, the warning component can be operable to issue an alert to the user if the number of pills 12 on the tray 14, as determined based on a signal transmitted by the recognition device(s) and received by the controller 38, does not correspond to the number of pills 12 on the tray 14 determined based on the weight measured by the scale 42. As mentioned above, the approximate weight of an identified pill 12 can be retrieved by the controller 38 from the appropriate drug entry in the drug database, can be weighed by the user and entered into the identifying system 10 either manually or automatically by placing a single pill 12 on the scale 42, or determined and/or entered in any other manner. If the signal transmitted by the recognition device(s) 18, upon being interpreted by the controller 38, indicates that X pills 12 are present on the tray 14, but the controller 38, based on the weight measured by the scale 42, determines that Y pills 12 are present (X and Y are different weights), the warning component can issue a warning to bring this discrepancy to the user's attention.

According to an alternate embodiment, the user can optionally input the desired number of pills 12 to be dispensed to the patient into the controller 38 via the user interface 40, a computer peripheral such as a keyboard and/or mouse, or any combination thereof. Yet other embodiments can include using a scanner 44 to interrogate a machine-readable code on a prescription form prepared by, or on behalf of a prescribing physician to extract the number of pills 12 to be dispensed to the patient. Regardless of how the desired number of pills 12 to be dispensed is entered into the controller 38, the warning component can optionally compare this desired number to the number of pills 12 actually on the tray 14 based on the signal from the recognition device(s), based on the weight of the pills 12 and the known weight of each pill as described elsewhere herein, or any combination thereof. The warning component can issue an alert until the actual number of pills 12 on the tray 14 matches the desired number to be dispensed, or issue an alert once the actual number of pills 12 on the tray 14 matches the desired number to be dispensed.

The warning component can be operable to issue an alert to the user under other circumstances based on information determined by the controller 38 from the identifying feature(s) of the pills 12 alone, as detected by the recognition device(s). For example, the warning component can issue an alert if the identity of the medicinal substance is not determinable based on the identifying feature(s) detected by the recognition device(s) (e.g., a matching drug entry could not be found in the drug database). The alert can be issued if the identifying feature(s) detected by the recognition device(s) 18 do not uniquely identify the medicinal substance (e.g., a plurality of different drug entries in the drug database contain identifying feature(s) that match those detected by the recognition device(s) 18). The alert can be issued if the pills 12 on the tray 14 include a first pill 12*a* formed at least in part from one medicinal substance (e.g., oxycodone) and a second pill 12*b* formed at least in part from another medicinal substance (e.g., acetaminophen/hydrocodone). As another example, the alert can be issued if the pills 12 on the tray 14 include pills with different dosages of the same, or a different, medicinal substance (e.g., a first pill 12*c* contains 10 mg of oxycodone and a second pill 12*d* contains 50 mg of oxycodone).

According to another embodiment, the warning component can be operable to issue an alert to the user if any portion of the information encoded by the barcode 56 on the patient label 54 does not match any corresponding portion of information available to the identifying apparatus 10. For example, once the patient container 52 has been filled and the label 54 bearing the barcode 56 has been printed by the printer 50, the barcode can be scanned by the scanner 44. The controller 38 can interpret a signal generated in response to interrogation of the barcode 56 to extract the information encoded by the barcode 56, and compare that information to information determined based on the identifying feature(s) of the pills 12 on the tray 14, or determined in any other manner. The warning component can issue the alert if any of the compared information does not match.

Figure 4A:
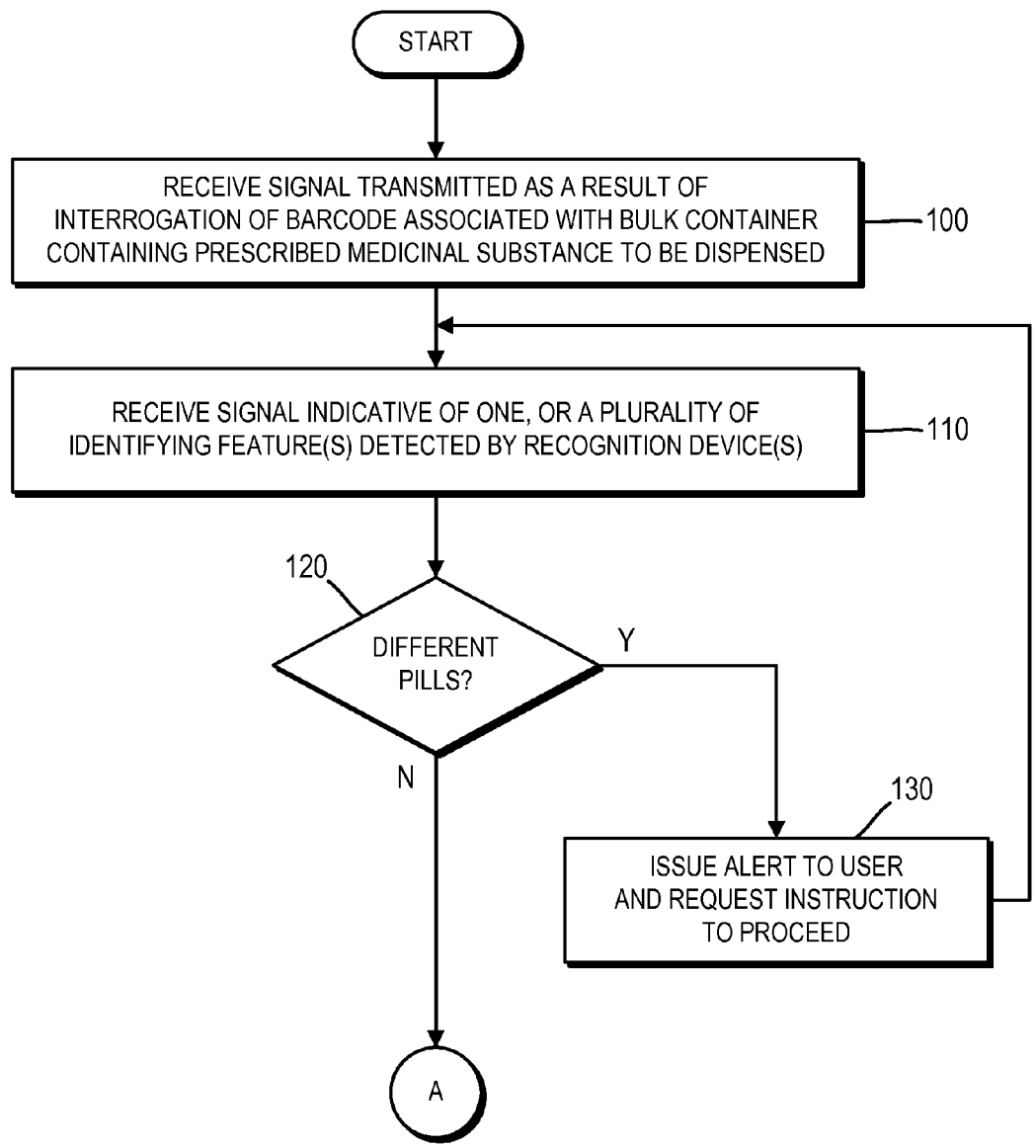
FIGS. 4A-4E include a flow diagram graphically depicting a method according to an aspect of the present invention.

Use of the identifying system is explained with reference to FIGS. 4A-4E. In FIG. 4A, the barcode 48 (FIG. 1) provided to the bulk container 46 is interrogated by the scanner 44 and the resulting signal indicative of the encoded information is received by the controller 38 at step 100. Once the pills 12 have been placed on the tray 14, the plurality of recognition devices 18*a*, 18*b* in this example capture identifying feature(s) of each pill 12 on the tray 14 from vantage points above and below the tray 14. Capturing the identifying feature(s) from both vantage points allows for the imprint 24 (FIGS. 2 and 3) or other markings on each side of the pills 12 to be captured. The controller 38 receives signal(s) indicative of the identifying feature(s) detected by the recognition devices 18*a*, 18*b* at step 110, and determines whether a plurality of different pills 12 are present on the tray 14 at step 120.

The controller 38 can receive identifying feature(s) for each of the pills 12 present on the tray 14. Thus, if there are five (5) total pills 12 present, the controller 38 can receive information indicative of the identifying feature(s) detected for each pill 12. Thus, the controller 38 can readily determine whether at least one pill 12 an identifying feature that is different than an identifying feature of another one of the pills 12 on the tray 14. If so, the warning component issues an alert at step 130 to bring the possible existence of an undesired pill 12 on the tray 14 and requests the user to inspect the pills 12 in an attempt to address this discrepancy. The process returns to step 110 to again receive the signal(s) from the recognition devices 18*a*, 18*b* indicative of the identifying feature(s) detected.

Figure 4B:
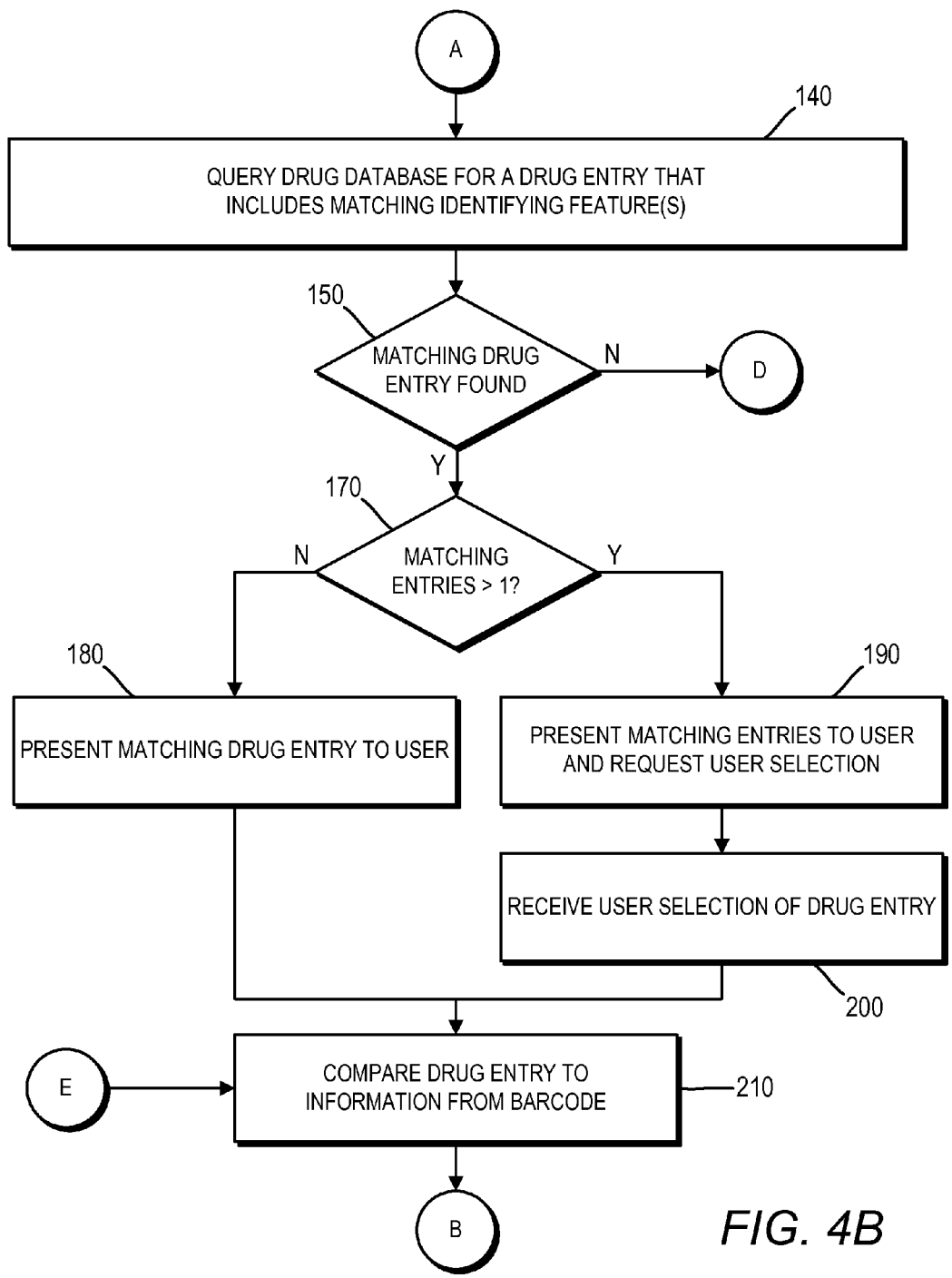
Figure 4C:
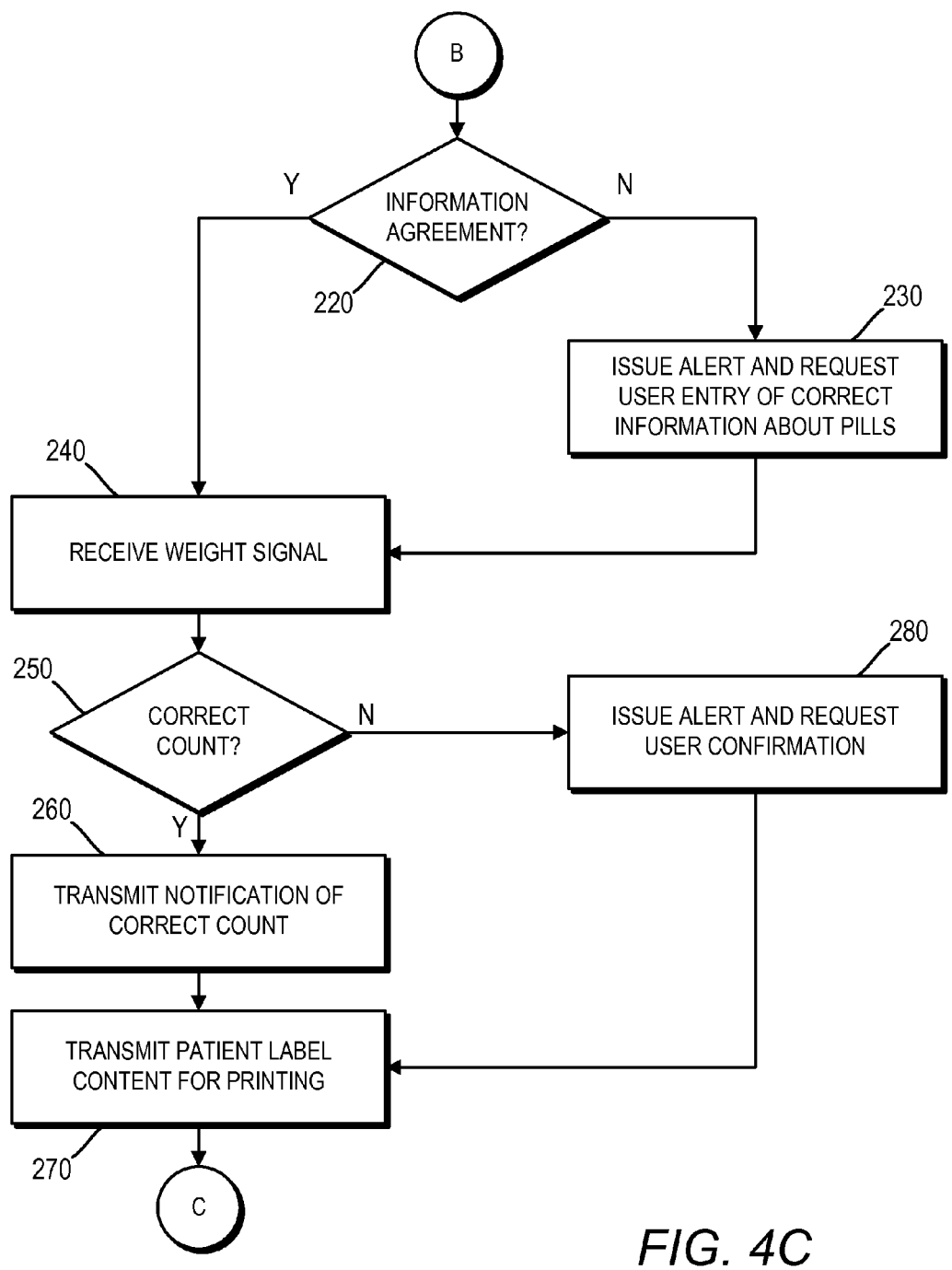

If all of the pills 12 on the tray 14 exhibit the same identifying feature(s) as determined at step 120, the process continues to step 140 shown in FIG. 4B, where the detected identifying feature(s) are used to query the drug database for drug entries with the same identifying feature(s). If it is determined at step 150 that no matching drug entries contain the identifying feature(s) detected by the recognition devices 18*a*, 18*b*, the warning component issues an alert, at step 160 in FIG. 4E, to the user, indicating that no drug entries were found in the database with the same identifying feature(s) as those detected by the recognition devices 18*a*, 18*b*. In other words, there was not a drug entry with at least a minimum number of the identifying features captured by the recognition devices 18*a*, 18*b* to establish a match with reasonable certainty.

If, on the other hand, it is determined at step 150 in FIG. 4B that at least one matching drug entry containing the identifying feature(s) detected by the recognition devices 18*a*, 18*b* (or at least more than a minimum number of those recognition features to establish a match with reasonable certainty) has been found in the drug database, it is then determined at step 170 whether the identifying feature(s) detected by the recognition devices 18*a*, 18*b* uniquely identify only a single matching drug entry, or whether more than one matching drug entry has been found. If only one matching drug entry is returned, the matching drug entry can optionally be presented to the user at step 180 for confirmation purposes. If more than one matching entry exists, the controller 38 can present each of the matching entries returned via the user interface 40 at step 190, and receive a user-input selection of the appropriate drug entry at step 200 from those presented.

Once the correct medicinal substance in the pills 12 has been received, the information pertaining to the medicinal substance, such as identity, dosage, any other pertinent information, or any combination thereof can optionally be compared, at step 210, to the corresponding information obtained based on the signal received at step 100 in FIG. 4A. If it is determined at step 220 in FIG. 4C that the compared information is not in agreement (i.e., there is conflicting information such as different identities, doses, both, etc. . . . ), the warning component issues an alert at step 230 and requests the user to manually enter information that resolves the conflict.

Before, after or during receipt of the conflict-resolving information requested at step 230, or the determination that no conflict exists at step 220, a weight signal transmitted by the scale 42 indicative of the overall weight of all pills 12 present on the tray 14 can optionally be received by the controller 38 at step 240. The controller 38 can determine at step 250 whether the number of pills 12 on the tray corresponds to a desired number of pills 12 to be dispensed to the patient based on at least one of the weight signal received at step 240 and the signal(s) indicative of the identifying feature(s) received at step 110 (as explained above, the number of pills 12 can also be determined based on the signal from the recognition devices 18*a*, 18*b*). If so, a notification can optionally be presented to the user indicating that the desired number of pills 12 is present on the tray 14 at step 260. Accordingly, the user can then transfer all of the remaining pills 12 on the tray to the patient container 52 with confidence that the number of pills 12 is correct. The patient label content that is to appear on the patient label 54 to be applied to the patient container 52 can also be transmitted to the printer 50 at step 270 for printing.

If, at step 250, it is determined that the number of pills 12 on the tray is incorrect, an alert and a request for the user to confirm the accuracy of the number of pills 12 on the tray 14 can be issued at step 280, before the process continues by transmitting the patient label content to the printer 50 at step 270.

Figure 4D:
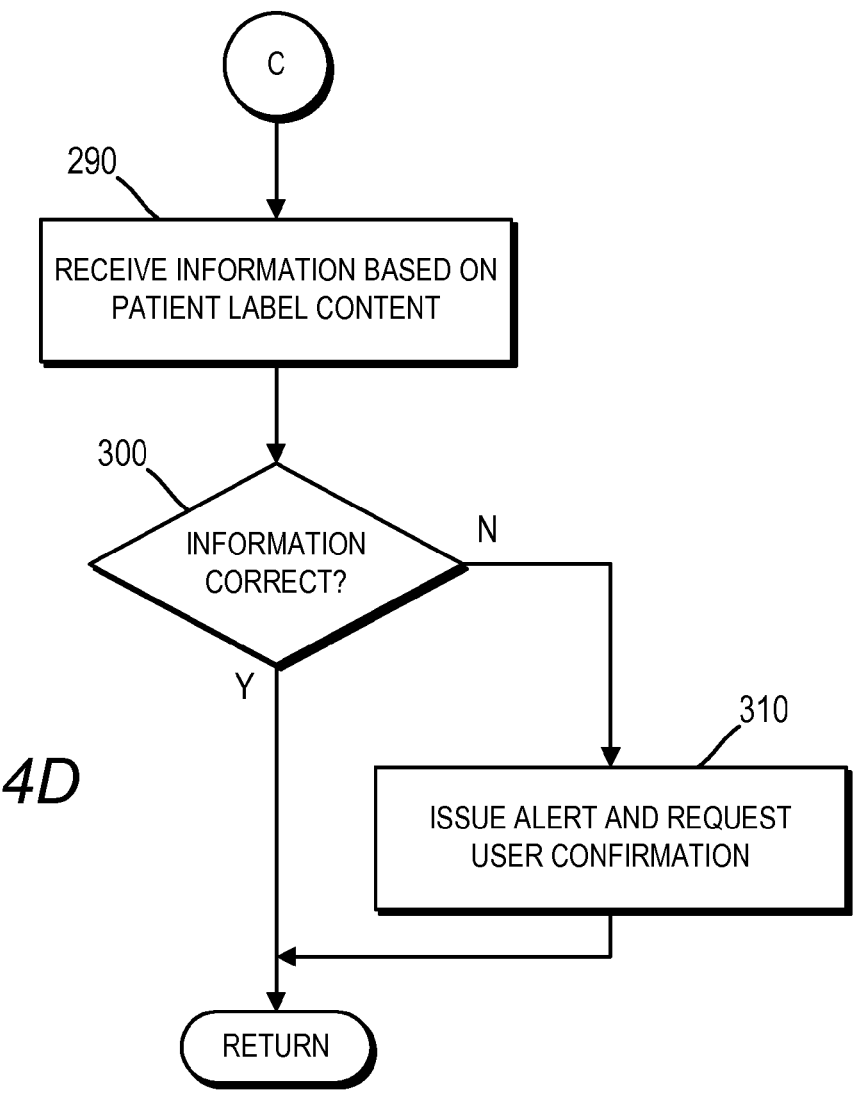
Figure 4E:
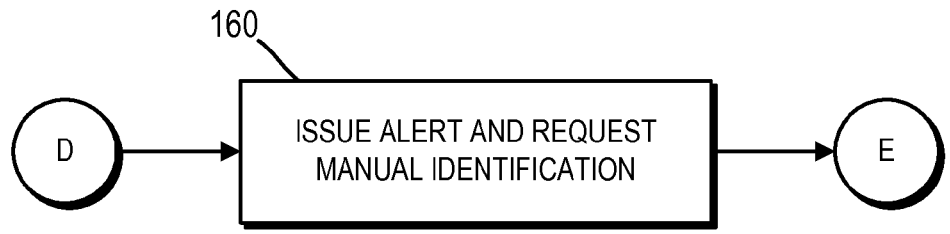

At step 290 in FIG. 4D, a signal can optionally be received by the controller 38 as a result of interrogating the patient label content, which can include the barcode 56, with the barcode scanner 44. The information obtained by interrogating the barcode 56 included in the patient label content can be compared against any of the information pertaining to the pills 12 described herein for consistency at step 300. If this information is consistent with the information against which it is compared, the process is completed, otherwise the warning component issues an alert at step 310, optionally requesting user confirmation of the patient label content, before returning.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An apparatus for identifying a medicinal substance, the apparatus comprising:
    a tray that receives and concurrently supports a plurality of individual pills removed from a bulk container, the individual pills being formed at least in part from the medicinal substance that have been removed from the container;
    a non-transitory computer-readable memory storing a drug database comprising a plurality of drug entries, wherein each drug entry comprises at least one physical property related to an identity of a pill formed at least in part from a different medicinal substance;
    a recognition system comprising one or more recognition devices that capture an image of a plurality of different surfaces of each of the plurality of individual pills removed from the container while arranged on the tray, wherein the recognition system, from the image, recognizes at least one identifying feature comprising a visible physical property of the individual pills on the tray from both an upward-facing surface of a fist pill resting on the tray and downward-facing surface of a second pill resting on the tray; and
    a controller that receives a signal indicative of the at least one identifying feature detected by the one or more recognition devices for the first pill and second pill and determines at least one possible identity of the medicinal substance forming the first pill and the second pill from among the different medicinal substances in the drug database based on the at least one identifying feature detected by the one or more recognition devices from the upward-facing surface of the first pill and the downward-facing surface of the second pill.

2. The apparatus of claim 1 further comprising a scanner that interrogates a machine-readable code associated with the container from which the plurality of individual pills to be identified are removed, wherein
    a signal indicative of the machine-readable code transmitted by the scanner in response to interrogating the machine-readable code is processed by the controller to identify the medicinal substance included in the individual pills.

3. The apparatus of claim 2 further comprising a warning component that issues an alert when conflicting medicinal substances are identified based on the at least one identifying feature recognized by the recognition system and based on interrogation of the machine-readable code.

4. The apparatus of claim 1 further comprising a scale that weighs the individual pills on the tray and transmits a weight signal indicative of a weight of the individual pills on the tray to the controller.

5. The apparatus of claim 4, wherein the recognition system detects a number of the individual pills present on the tray as a result of observation of the pills and transmits a quantity signal indicative of the number of the individual pills to the controller.

6. The apparatus of claim 5, wherein the controller processes the weight signal and the quantity signal to determine whether the weight of the individual pills on the tray determined using the scale is consistent with the number of the individual pills on the tray determined using the recognition device, and issues a warning if the weight of the individual pills is not consistent with the number of the individual pills on the tray.

7. The apparatus of claim 1, wherein at least one of the one or more recognition devices comprises:
    an illumination source that emits light having a plurality of different wavelengths to be imparted onto the pills on the tray; and
    a sensor that senses a response of the pills to being illuminated by light having the plurality of different wavelengths.

8. The apparatus of claim 1, wherein at least a portion of the tray is formed from a material that is substantially transparent to at least one of the one or more recognition devices to allow for observation of the pills on the tray through the substantially transparent material by the at least one of the recognition devices.

9. The apparatus of claim 8, wherein the recognition system comprises:
    a first recognition device to be arranged at an elevation vertically above the tray to observe the pills on the tray from above; and
    a second recognition device to be arranged at an elevation vertically below the tray to observe the pills on the tray through the portion formed from the material that is substantially transparent to the second recognition device from below.

10. The apparatus of claim 1 further comprising a marking system provided to the tray in a manner that is detectable by the recognition system, wherein the marking system provides the recognition system with a reference for detecting the visible physical property of the individual pills on the tray.

11. The apparatus of claim 10, wherein the marking system comprises a grid pattern that forms a reference for optically measuring at least one of a size and a shape of the individual pills on the tray.

12. The apparatus of claim 1, wherein the recognition system comprises a camera that captures an image of the individual pills on the tray, and the controller analyzes the image to determine at least one of: a size of the individual pills, a shape of the individual pills, a color of the individual pills, and a character visible on a surface of the individual pills.

13. The apparatus of claim 1 further comprising a printer for printing a patient label to be applied to a container in which at least a portion of the individual pills on the tray are to be conveyed to a patient, wherein the printer prints label content comprising a computer-readable code onto the patient label, wherein the computer-readable code printed by the printer encodes an identity of the medicinal substance as determined by the controller based on the at least one identifying feature detected by the recognition system.

14. The apparatus of claim 13 further comprising:
a user interface that can output information to a user;
a scanner that is operable to interrogate the computer-readable code on the patient label and transmit a signal to the controller to be processed and used to generate a confirmation notice that is to be output by the user interface to the user to notify the user of a medicinal substance identified by the computer-readable code; and
a warning component that issues a warning to the user when the medicinal substance identified by the computer-readable code does not match the identity of the medicinal substance determined based on the at least one identifying feature detected by the recognition device.

15. The apparatus of claim 1 further comprising a warning component that issues an alert to a user if at least one condition is determined to exist by the controller, wherein the condition is selected from a group consisting of:
the identity of the medicinal substance is not determinable based on the at least one identifying feature detected by the recognition device;
the at least one identifying feature detected by the recognition device corresponds to more than one of the different medicinal substances in the drug database;
the pills on the tray comprise a first pill formed at least in part from a first medicinal substance and a second pill formed at least in part from another medicinal substance; and
the pills on the tray comprise pills with different dosages of the medicinal substance.

16. The apparatus of claim 1, wherein the recognition system detects a plurality of identifying features from the individual pills on the tray and transmits a signal indicative of the plurality of identifying features to the controller to be compared by the controller to the plurality of identifying features stored in the drug database for identifying the at least one possible identity of the medicinal substance.

17. The apparatus of claim 16, wherein at least one of the plurality of identifying features detected by the recognition system is detected from each of the different surfaces.

18. The apparatus of claim 1, wherein the at least one identifying feature detected by the recognition system comprises a feature found on the individual pills as received from a source of the pills.

19. An apparatus for identifying a medicinal substance, the apparatus comprising:
a tray that receives and concurrently supports a plurality of individual pills formed at least in part from the medicinal substance that have been removed from a container;
a non-transitory computer-readable memory storing a drug database comprising a plurality of drug entries, wherein each drug entry comprises at least one physical property related to an identity of a pill formed at least in part from a different medicinal substance;
a recognition system comprising one or more recognition devices that captures an image of a plurality of different surfaces of each of the plurality of individual pills arranged on the trayand, from the image, recognizes at least one identifying feature comprising a visible physical property of the individual pills on the tray;
a controller that receives a signal indicative of at least one identifying feature detected by the one or more recognition devices and determines at least one possible identity of the medicinal substance from among the different medicinal substances in the drug database based on the at least one identifying feature detected by the one or more recognition devices;
a scanner that interrogates a machine-readable code associated with the container from which the plurality of individual pills to be identified are removed, wherein a signal indicative of the machine-readable code transmitted by the scanner in response to interrogating the machine-readable code is processed by the controller to identify the medicinal substance included in the individual pills; and
a warning component that issues an alert when conflicting medicinal substances are identified based on the at least one identifying feature recognized by the recognition system and based on interrogation of the machine-readable code.

\* \* \* \* \*